United States Patent [19]

Urban

[11] Patent Number: 5,064,994

[45] Date of Patent: Nov. 12, 1991

[54] FAST-HEATING HIGH-TEMPERATURE FIBER CUTTING TOOL

[76] Inventor: Paul L. Urban, 209 Funderburk Dr., Cheraw, S.C. 29520

[21] Appl. No.: 423,060

[22] Filed: Oct. 18, 1989

[51] Int. Cl.$^5$ .............................................. H05B 1/00
[52] U.S. Cl. .................................... 219/233; 219/221; 219/227; 219/229; 83/171; 30/345
[58] Field of Search ............... 219/233, 221, 227, 230, 219/229, 234, 236, 238, 203, 239, 10.81, 10.77, 10.43, 10.53, 240, 243; 83/15, 16, 170, 171; 30/140, 345, 286; 139/429, 302, 450; 337/407, 403; 307/326, 45; 606/37, 39, 40, 45, 48, 50, 49, 42

[56] References Cited

U.S. PATENT DOCUMENTS

| | | | |
|---|---|---|---|
| 2,200,322 | 5/1940 | Arnesen | 219/233 |
| 2,863,036 | 12/1958 | Mitchell et al. | |
| 4,031,431 | 6/1977 | Gross | 307/326 |
| 4,139,760 | 2/1979 | Banks | 219/227 |
| 4,850,353 | 7/1989 | Stasz et al. | 606/37 |

*Primary Examiner*—Bruce A. Reynolds
*Assistant Examiner*—Tu Hoang
*Attorney, Agent, or Firm*—Kenyon & Kenyon

[57] ABSTRACT

A fiber cutting tool is disclosed which comprises a heated element cartridge and a body. The heated element cartridge comprises (a) a blade formed from a fast heating resistance heating element encased in a thermal shock resistant and electrical resistant material, such blade having a distal end and a proximate end; (b) an element cover having a distal end and a proximate end which encloses the proximate end of the blade; and (c) a cartridge housing that encloses a portion of the proximate end of the element cover. In preferred embodiments, the blade is formed from a tungsten resistance heating element encased in a silicon nitride composite material. The body comprises (a) a body housing forming a handle; (b) a power supply for supplying power to components mounted within the housing; (c) a trigger switch mounted within the housing for activating the tool; (d) a setting switch mounted within the housing for specifying the desired temperature setting of the blade; and (e) a socket mounted within the housing and adapted for receiving the heated element cartridge. The power supply, trigger switch, setting switch and socket are electrically connected such that when the trigger switch is activated power is conveyed from the power supply to the resistance heating element causing the blade to heat to the desired temperature setting.

9 Claims, 4 Drawing Sheets

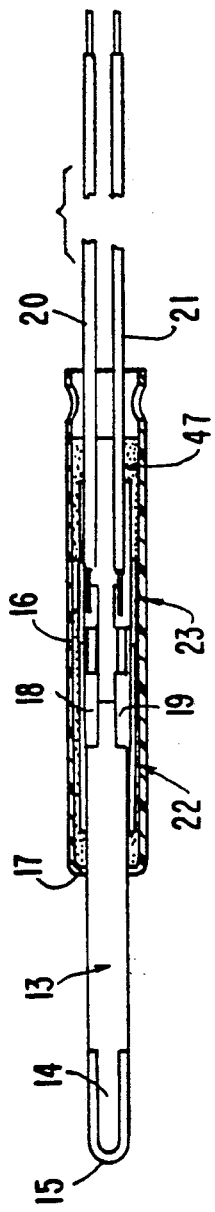
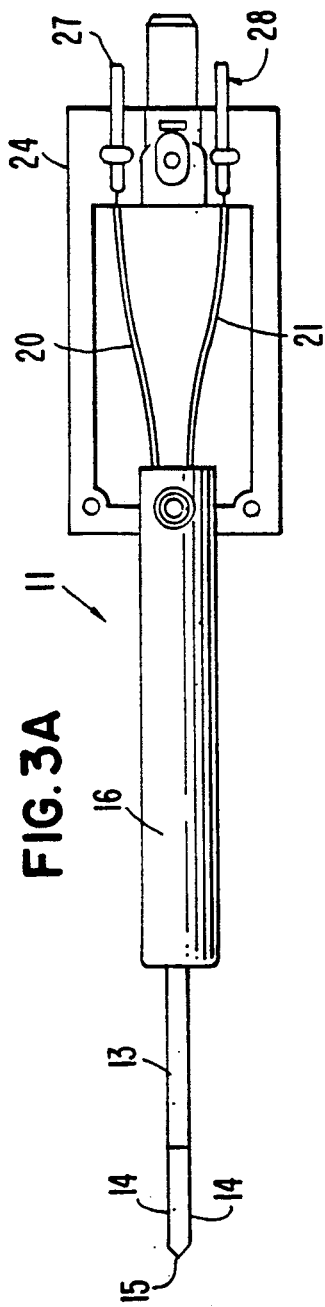
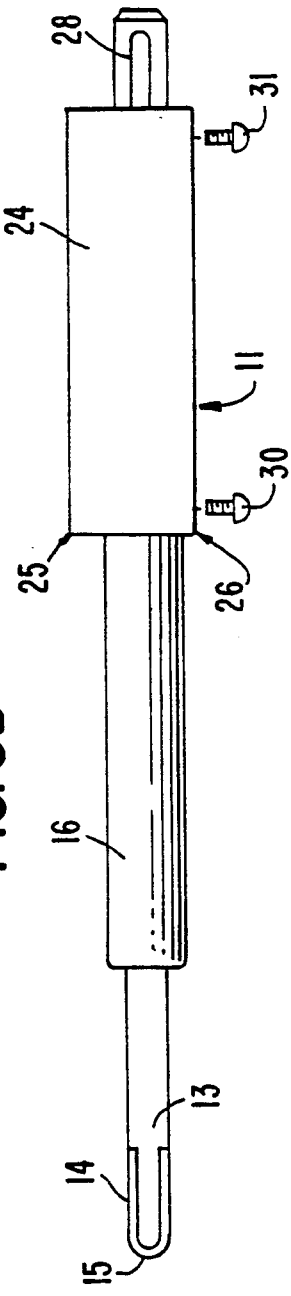
FIG. 2
FIG. 3A
FIG. 3B

FAST-HEATING HIGH-TEMPERATURE FIBER CUTTING TOOL

FIELD OF THE INVENTION

The present invention relates to heated tools for cutting fiber, particularly to hand held fast-heating high temperature devices for cutting fiber from spools, rolls or other fiber gathering means, which incorporate a heated element made by encapsulating a resistance heating element with a thermal and electrical resistant material.

BACKGROUND OF THE INVENTION

Many industrial applications require cutting of natural or synthetic fibers, or materials made from such fibers, from spools, rolls or other means for gathering the fiber or fiber material. Fiber cutting is mostly commonly required in the textile and other industries where fiber and fiber materials are woven or spun and then wound onto spools or rolls for handling. Although a conceptually simple operation, efficient fiber cutting has proven difficult in certain manufacturing contexts.

Cutting fiber manually with a knife or other sharp implement is often not practical. Manual cutting requires excessive physical effort by the cutter, especially when the material being cut is unusually thick or extends over a significant distance. Many fiber materials, such as glass or plastic fibers, are resistant to cutting by hand held blades, thus making manual cutting even more difficult.

Cutting tools, similar to heavy duty soldering tools, that employ a heated cutting tip have more recently been used. Such tools burn or melt the fiber material, allowing the cutter to cut the fiber more quickly as compared to the more traditional cutting knife. Fiber materials resistant to a manually operated cutting knife can be more easily cut with the heated tool.

However, such heated cutting tools have exhibited several disadvantages of their own. Many of such tools employ copper cutting tips which are easily deformed, especially at high temperature, and as a result do not hold up well in use. Tools employing copper tips are also relatively useless at temperatures above about 1100° F. because the copper tips become so soft that only a little pressure can be applied to the tip, thus making cutting slower and more difficult. This temperature limitation also renders such tools virtually useless for cutting fiber material which does not burn or melt at the highest temperature allowed by such tools.

Previous heated cutting tools also place some physical strain on the user because such devices tend to be relatively heavy (1-2 pounds) largely due to the weight of the transformers. Over extended periods of use, the heavy devices cause significant user fatigue. Breakage is also increased because dropping such devices often results in greater damage. Finally, devices incorporating transformers are also prone to "burning out" upon extended or continuous use.

It would, therefore, be desirable to provide a fiber cutting tool which provides the benefit of a heated cutting element in a light weight form and which provides the added benefits of very high temperatures and prolonged tool life.

SUMMARY OF THE INVENTION

The apparatus of the present invention overcomes the disadvantages noted above with a unique combination of elements. As described with respect to the preferred embodiment, a cutting tool is disclosed which comprises a heated element cartridge and a body. The heated element cartridge comprises (a) a blade having a distal end and a proximate end, said blade comprising a resistance heating element at least partially encapsulated by or surrounded by an insulating, thermal shock resistant and electrical resistant material; (b) an element cover, having a distal end and a proximate end, which encloses the proximate end of the blade; (c) a cartridge housing that encloses a portion of the proximate end of the element cover; and (d) leads connected to the blade, and extending to the exterior of the cartridge, for providing current to the resistance heating element. In preferred embodiments, the resistance heating element is formed from commonly-known resistive materials, such as tungsten, by known means and is then encased in silicon nitride.

The body comprises (a) a body housing forming a handle; (b) a power supply for supplying power to components mounted within the housing; (c) a trigger switch mounted within the housing for activating the tool; (d) a setting switch mounted within the housing for specifying the desired temperature setting of the blade; and (e) a socket mounted within the housing and adapted for receiving the heated element cartridge and for making electrical contact with the leads from the heated element cartridge. The power supply, trigger switch, setting switch and socket are electrically connected such that, when the trigger switch is activated, power is conveyed from the power supply to the resistance element in the blade through leads, thus causing the blade to heat to the desired temperature setting.

The discussion above relates some disadvantages of the prior art and features of the invention. Other advantages will be apparent from the detailed discussion of the preferred embodiment which follows.

BRIEF DESCRIPTION OF THE FIGURES

FIG. 2 is a side cutaway view of the heated element cartridge of the preferred embodiment.

FIG. 3A is a top elevation of the heated element cartridge of the preferred embodiment with the top half of the cartridge housing removed to show internal components and wiring.

FIG. 3B is a side elevation of the assembled heated element cartridge of the preferred embodiment.

DETAILED DESCRIPTION OF THE INVENTION

Figure 1:
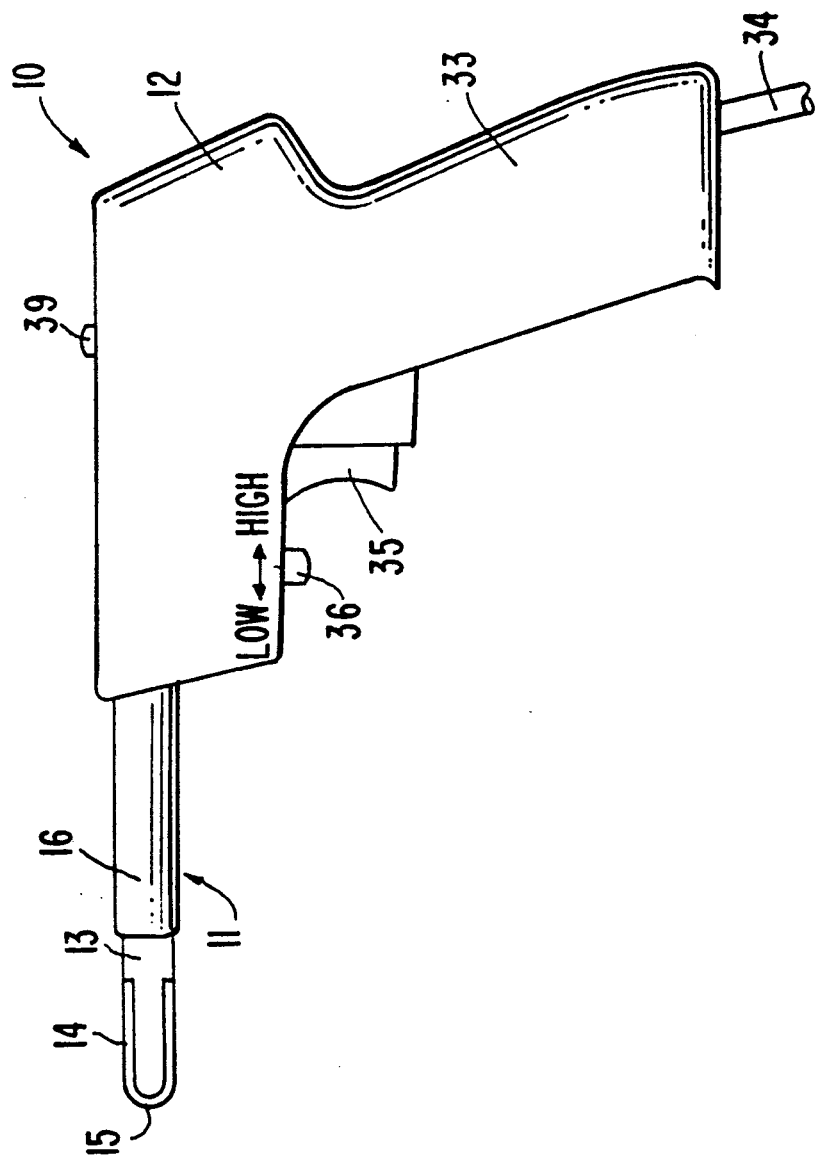
FIG. 1 is a side elevation of the preferred embodiment of the fiber tool of the present invention.

The preferred embodiment of fiber cutting tool 10 of the present invention comprises heated element cartridge 11 and body 12.

The cutting surface of heated element cartridge 11 is blade 13 which has a proximate end and a distal end. Blade 13 comprises a resistance heating element formed from a "fast heating" resistive material, such as tungsten, which is encased in thermal shock resistant and electrical insulating materials, such as alumina ceramics or silicon nitride. Silicon nitride is preferred. It is also desirable that the encapsulating material is chemically resistant, is abrasion resistant, does not become weak at the operating temperature of the device, and provides good insulation resistance and thermal conductivity. The distal end of blade 13 may be machined to take any desired shape or form suitable to the application for which the tool is fashioned.

In one preferred embodiment blade 13 is formed from a tungsten resistance element surrounded by silicon nitride. The resulting blade has the chemical and physical characteristics summarized in Table I.

TABLE I

| Material | resistive element: tungsten encapsulation material: silicon nitride |
|---|---|
| Maximum Use Temperature | 1350° C. (2462° F.) |
| Continuous Use Temperature | 1200° C. (2192° F.) |
| Time to 1000 F (Full Power) | 12 seconds |
| Thermal Conductivity | 0.04 cal cm/cm$^2$ sec °C. |
| Specific Heat | 0.16 cal/g °C. |
| Coefficient of Linear Thermal Expansion | 3.2 × 10$^{-6}$/°C. (40 to 800° C.) |
| Specific Electrical Resistance | $R_T = (1.75 \times T/1000 + .09558)R_{25}$ $R_T$ = Specific Electrical Resistance at temperature T° C. T = Temperature of heater, °C. $R_{25}$ = Resistance of heater at 25° C. |
| Chemical Resistance: | Weight Reduction (after 30 min. boiling) |
| Sulfuric Acid 95% | 0.13 mg/cm$^2$ |
| Nitric Acid 60% | 0.14 mg/cm$^2$ |
| Sodium Hydroxide 30% | 0.17 mg/cm$^2$ |

As shown in FIGS. 1-3, the distal end of blade 13 of the preferred embodiment is machined to form beveled surfaces 14 which form cutting edge 15 which facilitates better fiber cutting.

The proximate end of blade 13 is encased in a generally round element cover 16 formed of type 304 Stainless Steel. Blade 13 is inserted into the distal end of element cover 16 through hole 17. Blade 13 is attached to terminals 18 and 19, which are in turn welded to supply leads 20 and 21 which extend out through the proximate end of element cover 16 and supply current to the resistance heating element. A portion of the proximate end of blade 13 and the junction of terminals 18 and 19 and supply leads 20 and 21 are surrounded by a double layer of mica 22 for insulation purposes and a band of tape 23 for securing the mica in place. Most of the remaining space within element cover 16 is filled with ceramic powder 47 to secure the blade within the element cover.

The previously described assembly including blade 13 and element cover 16 are combined with cartridge housing 24 to complete the preferred embodiment of heated element cartridge 11. Cartridge housing 24 is constructed in two halves 25 and 26 from high temperature thermoplastic or thermoset plastics. The proximate end of element cover 16 is inserted through holes in the distal end of cartridge housing 24. Supply leads 20 and 21 are then connected to supply pins 27 and 28 which extend from the proximate end of cartridge housing 24 for connection to an electrical power source. The halves of cartridge housing 24 are joined by anchor screws 30 and 31 which also serve to hold element cover 16 in place.

Figure 4B:
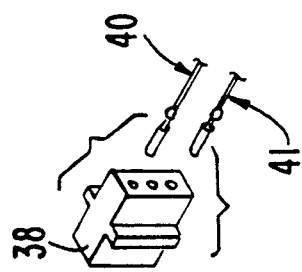
FIG. 4B is a perspective view of the heated element cartridge socket of the preferred embodiment and leads thereto from the circuit board.
Figure 4A:
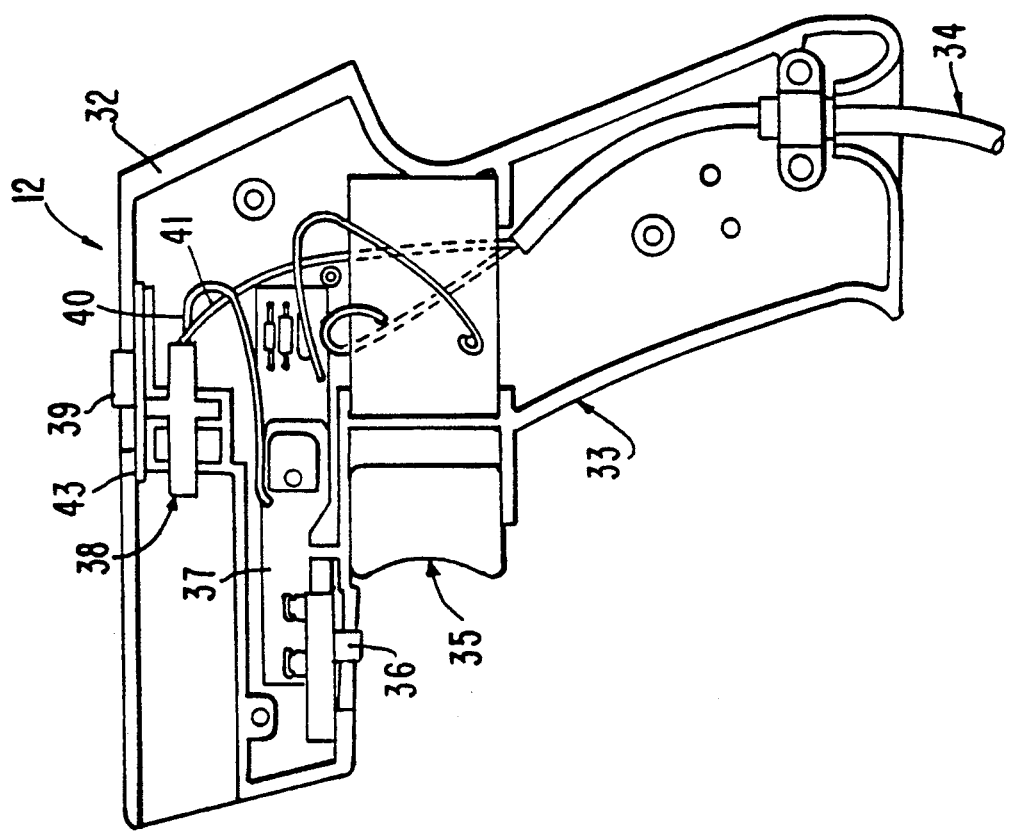
FIG. 4A is a side cutaway view of the body of the preferred embodiment with one-half of the body housing removed to show internal components and wiring.

Body 12 is formed by body housing 32 which is constructed in two halves having a generally symmetrical configuration and fixed to one another in a convenient manner. In FIG. 4A, one half has been removed to reveal the components contained in body 12. Body housing 32 forms handle 33 adapted for insertion of power cord 34 (supplying 120 volts, 60 Hz in the preferred embodiment). Trigger switch 35, setting switch 36, circuit board 37, cartridge socket 38 and eject button 39 are mounted within body 12 and are connected in the manner shown in FIG. 4 and in the schematic in FIG. 5.

Figure 5:
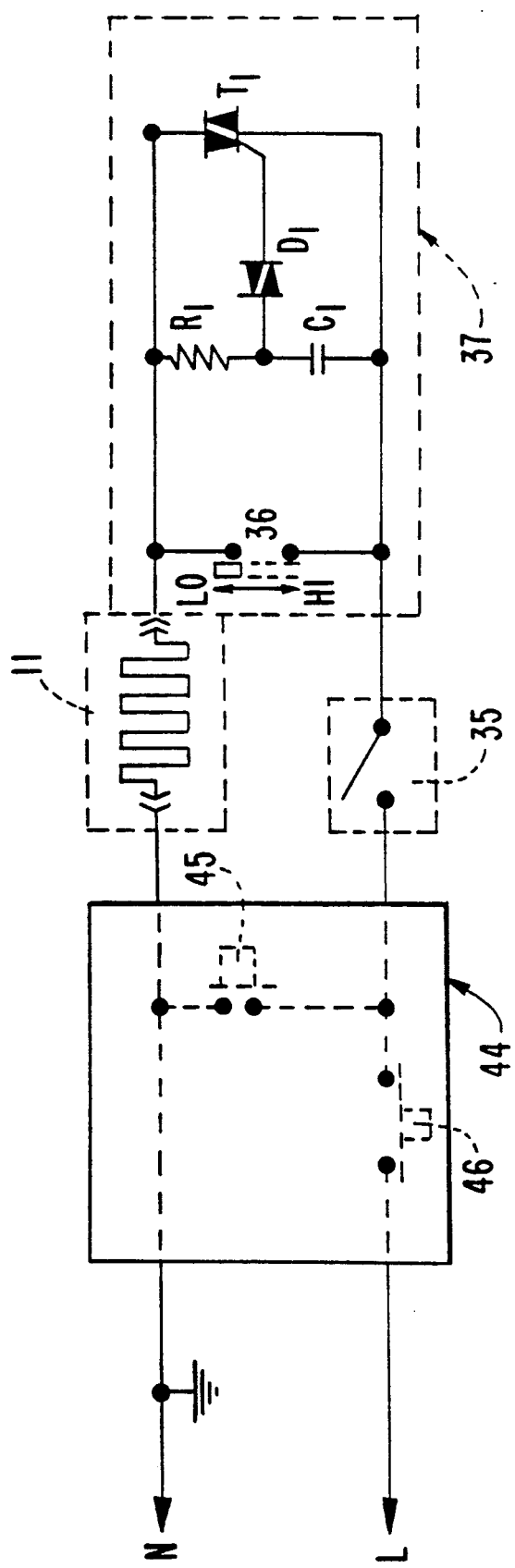
FIG. 5 is a schematic diagram of the circuit of the preferred embodiment.

Trigger switch 35 controls the supply of power to the heated element and is of the type commonly used in heavy duty soldering guns. Setting switch 36 toggles between two positions corresponding to a "low temperature" setting and a "high temperature" setting. As shown in FIG. 5, in the preferred embodiment, the high temperature setting bypasses the other components of circuit board 37, thus delivering more current to blade 13 resulting in a higher blade temperature. In the preferred embodiment employing the blade material described in Table I above, the high temperature setting applies full power to the heated element and allows the blade to reach 1800°-2200° F. in 12 seconds. The low temperature setting applies half power and allows the blade to reach 900°-1100° F. in 15 seconds.

Cartridge socket 38 is adapted for receiving supply pins 27 and 28. Leads 40 and 41 are housed within cartridge socket 38 such that, when the heated element cartridge 11 is inserted into cartridge socket 38, supply pins 27 and 28 contact leads 40 and 41 to complete the circuit as shown in FIG. 5.

Eject button 39 has a flange 43 which extends toward the proximate end of cartridge housing 24 when heated element cartridge 11 is inserted into body 12 and cartridge socket 38. When eject button 39 is pushed toward blade 13, flange 43 abuts with cartridge housing 24 and disengages heated element cartridge 11 from cartridge socket 38. In this way, the cartridge can be removed and exchanged without touching the hot surfaces of the cartridge.

The preferred embodiment is also provided with a Ground Fault Circuit Interrupter GFCI 44 located in a plug (not shown) on supply cord 34 for protecting the user from accidental electrical shocks. The GFCI is designed to remove power from equipment loads when the loads have a potentially lethal ground current in excess of six milliamperes. The GFCI does not limit the magnitude of the ground fault current. It simply limits the time that a current of given magnitude can flow. The GFCI used in the preferred embodiment is designed so that it will automatically trip if the neutral conductor is grounded on the load side of the current sensor. When the GFCI trips, both the hot and neutral lines are broken preventing any possible current flow or injury to the user. The GFCI is provided with a test button 45 which checks the trip level of the GFCI. A simulated ground fault is applied to the sensing circuit (not shown) through a resistor when test button 45 is depressed. The GFCI is also provided with reset button 46 for resetting the protective circuit. Alternatively, the GFCI can be eliminated and the cutting tool can be constructed employing a simple ground from the heating element cover to a third wire ground in the power cord, utilizing another pin, like pin 27, to make the electrical connection between the cartridge and the handle.

Additional specifications for the preferred embodiment described herein are summarized in Table II.

TABLE II

| Voltage | 120 VAC; 60 Hz |
|---|---|
| Wattage | 55 +/ 10 watts |
| Blade Temperature | high: 1800-2200 F. |
| | low: 900-1100 F. |
| GCFI Trip Level | 6.0 ma maximum leakage to ground |
| Weight (less cord and plug) | approximately 6 oz |

From the foregoing it will be apparent to those skilled in the art that various modifications in the above-described devices can be made without departing from the scope and spirit of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A cutting tool for cutting fibers comprising a heated element cartridge and a body, said body forming a handle, and said heated element cartridge comprising a blade, said blade comprising a resistance heating element encased in a material which is both thermal shock resistant and electrically insulating.

2. The cutting tool of claim 1 wherein said material is silicon nitride.

3. The cutting tool of claim 1 wherein said heated element cartridge further comprises an element cover enclosing the proximate end of said blade.

4. The cutting tool of claim 3 wherein said heated element cartridge further comprises a cartridge housing enclosing a portion of said element cover.

5. The cutting tool of claim 4 wherein said heated element cartridge further comprises leads connected to said resistance heating element and extending to the exterior of said heated element cartridge for connection to a power source.

6. The cutting tool of claim 1 wherein said material is alumina ceramic.

7. A cutting tool comprising a heated element cartridge and a body;
   (a) said heated element cartridge comprising:
      a blade having a distal end and a proximate end, said blade comprising a resistance heating element encased in a material which is both thermal shock resistant and electrically insulating;
      an element cover having a distal end and a proximate end, said distal end of said element cover enclosing said proximate end of said blade;
      a cartridge housing enclosing a portion of said proximate end of said element cover; and
      leads connected to said blade for providing current to said resistance heating element, said leads extending from said blade to the exterior of said heated element cartridge; and
   (b) said body comprising:
      a body housing forming a handle;
      a power supply for supplying power to components mounted within said housing;
      a trigger switch mounted within said housing for activating said tool;
      a setting switch mounted within said housing for specifying the desired temperature setting of said blade; and
      a socket mounted within said housing and adapted for receiving said heated element cartridge and for making electrical contact with said leads; and
   (c) wherein said power supply, said trigger switch, said setting switch and said socket are electrically connected such that when said trigger switch is activated power is conveyed from said power supply to said resistance heating element through said leads causing said blade to heat to said desired temperature setting.

8. The cutting tool of claim 7 wherein said material is silicon nitride.

9. The cutting tool of claim 7 wherein said material is alumina ceramic.

* * * * *